(12) United States Patent
Torris et al.

(10) Patent No.: US 8,172,808 B2
(45) Date of Patent: May 8, 2012

(54) TAMPER EVIDENT VACUUM TUBE HOLDER ASSEMBLY AND NEEDLE HUB ASSEMBLY THEREFOR

(75) Inventors: William T. Torris, Greer, SC (US); Glynn Clements, Greenville, SC (US); Gregory J. Brown, Simpsonville, SC (US)

(73) Assignee: Smiths Medical ASD, Inc., Keene, NH (US)

( * ) Notice: Subject to any disclaimer, the term of this patent is extended or adjusted under 35 U.S.C. 154(b) by 2256 days.

(21) Appl. No.: 10/419,934

(22) Filed: Apr. 22, 2003

(65) Prior Publication Data

US 2004/0211689 A1 Oct. 28, 2004

(51) Int. Cl.
*A61M 5/32* (2006.01)

(52) U.S. Cl. .................................. 604/192; 604/240

(58) Field of Classification Search .............. 604/110, 604/263, 579, 192–198, 181, 187, 240–243; 600/576; 206/366, 365

See application file for complete search history.

(56) References Cited

U.S. PATENT DOCUMENTS

| 3,073,307 | A | * | 1/1963 | Stevens | 604/192 |
| 4,927,019 | A | * | 5/1990 | Haber et al. | 206/365 |
| 5,277,311 | A | * | 1/1994 | Hollister | 206/365 |
| 5,823,997 | A | | 10/1998 | Thorne | |
| 5,980,488 | A | | 11/1999 | Thorne | |
| 6,027,482 | A | * | 2/2000 | Imbert | 604/256 |
| 2003/0028152 | A1 | * | 2/2003 | Alesi et al. | 604/240 |

* cited by examiner

*Primary Examiner* — Kevin C Sirmons
*Assistant Examiner* — Phillip Gray
(74) *Attorney, Agent, or Firm* — Louis Woo (57) ABSTRACT

A one piece molded vacuum tube holder is fitted with a one piece molded needle hub assembly. A needle protection device is further rotatably mounted to the neck of the one piece vacuum tube holder. One portion of a locking mechanism is provided at the neck of the one piece vacuum tube holder and a second portion of the locking mechanism is provided at the needle hub of the needle hub assembly, so that when the needle hub assembly is press fit to the vacuum tube holder, the two portions of the locking mechanism will coact to fixedly retain the needle hub assembly within the vacuum tube holder. The one piece vacuum tube holder is configured to have an elongate needle cover integrally extending from its neck. A tamper evident notched joint is provided at the junction where the needle cover is connected to the neck.

25 Claims, 5 Drawing Sheets

TAMPER EVIDENT VACUUM TUBE HOLDER ASSEMBLY AND NEEDLE HUB ASSEMBLY THEREFOR

FIELD OF THE INVENTION

The following invention relates to a device for holding a fluid container tube such as a vacuum tube, and particularly relates to a vacuum tube holder assembly that is readily manufactured, provides a built in tamper evident seal and has a needle protection housing that securely covers a contaminated needle after use.

BACKGROUND OF THE INVENTION

In U.S. Pat. No. 5,139,489 a vacuum tube holder has attached thereto a protective needle housing which is pivotable to cover an exposed needle of a double-ended needle assembly threaded to the vacuum tube holder. In U.S. Pat. No. 5,154,285, a needle protection housing is mounted to the neck of the vacuum tube holder by means of a collar, so that the housing is rotatable with respect to the neck of the vacuum tube holder. For both of the devices disclosed in the '489 and '285 patents, prior to use and shipping, the double-ended needle is capped at both ends.

Conventionally, a double-ended needle is shipped in a container that covers both ends of the needle. The container is taped with a piece of paper, or other sealing material, to provide evidence that it has not been tampered with prior to use. There has not been any tampering if there is no tear on the paper seal when a phlebotomist takes the double-ended needle out of the container and threads it to the vacuum tube holder or Vacutainer holder. Thus, to use the devices disclosed in the '489 and '285 patents, a user has to first remove the double-ended needle from its container and then thread the double-ended needle to the vacuum tube holder. Moreover, the user has to carry both the double-ended needle and the vacuum tube holder as separate units. The disclosures of the '489 and '285 patents are incorporated by reference herein.

SUMMARY OF THE PRESENT INVENTION

The present invention vacuum tube holder assembly is shipped as a single piece, with the various components pre-assembled. The vacuum tube holder is a molded one piece component that includes an elongate needle cover that integrally extends from the neck of the body of the vacuum tube holder. At the junction where the elongate needle cover meets the neck of the holder, there is a thinning out of material such as for example by a circumferential notching thereat. When a predetermined torque force is applied to the needle cover relative to either the neck or the body of the vacuum tube holder, the needle cover is readily removed or separated by the twisting motion. Once removed, the needle cover could not be reattached to the neck of the vacuum tube holder. Accordingly, a built in tamper evident seal is provided for the vacuum tube holder of the instant invention, in that a user knows that the vacuum tube holder has been tampered with if the needle cover is missing or is hanging loosely from the neck of the body of the vacuum tube holder.

A needle hub assembly specifically manufactured to be a component of the vacuum tube holder assembly is press fit through the opening of the vacuum tube holder body towards the neck of the vacuum tube holder. The needle hub of the needle hub assembly has a dimension that allows it to mate to the aperture of the neck of the vacuum tube holder which is smaller than the opening of the vacuum tube holder. At the needle hub of the needle hub assembly there are formed two catches that are movable transversely to the needle hub when biased. To enable the transverse movements for the catches, respective through slots are formed in the needle hub behind each of the catches. As the needle hub is press fit to the neck of the vacuum tube container, the catches would first compress, since they are in contact with upward sloping ramps at the inside wall of the neck, in order to pass the aperture of the neck. When the needle hub is pushed sufficiently far into the neck of the vacuum tube holder, openings or orifices formed on the opposite sides of the neck enable the catches, upon mating with those orifices, to return to their original shapes as they latch onto the orifices. Once the catches latch onto their respective orifices at the neck of the vacuum tube holder, the needle hub assembly is fixedly retained within the vacuum tube holder.

There is a raised boss or protuberance circumferentially formed at the outer surface of the neck of the vacuum tube holder. Rotatably mounted to the protuberance is a collar having an internal groove that mates to the protuberance. The tolerances provided for the internal groove of the collar and the protuberance about the neck of the vacuum tube holder during the molding process are such that the friction between the internal groove of the collar and the protuberance would hold the collar in place so long as an external torque force is not applied thereagainst. The collar is therefore not freely rotatable about the neck of the vacuum tube holder. Hingedly connected to the collar is a needle protection housing. Integral hooks are provided in the housing.

The vacuum tube holder assembly therefore includes the vacuum tube holder, the needle hub assembly fitted into the holder and the needle protection housing rotatably mounted to the neck of the vacuum tube holder. The opening at the end of the vacuum tube holder to which a vacuum tube or fluid container is insertable during use may be covered by a seal so that the vacuum tube holder assembly may be readily sterilized and shipped without any need for additional packaging.

BRIEF DESCRIPTION OF THE DRAWINGS

The present invention will become more apparent and the invention itself will be best understood by reference to the following description of the present invention taken in conjunction with the accompanying drawings wherein:

FIG. 1 is a cross-sectional view of the one-piece molded vacuum tube holder of the instant invention;

FIG. 3a is a semi-cross-sectional view of the FIG. 1 vacuum tube holder;

FIG. 3b is a bottom view looking into the cavity of the body of the vacuum tube holder of FIG. 3a;

FIG. 4 is an enlarged view of the semi-cross-sectional view of the neck of the vacuum tube holder shown in FIG. 3a;

FIG. 8a is a side view of a rubber boot to be fitted to the end of a double-ended needle that extends into the vacuum tube holder of FIG. 1;

FIG. 8b is a top view of the rubber boot shown in FIG. 8a;

FIG. 10 is an enlarged semi-cross-sectional view of the neck area of the inventive vacuum tube holder assembly.

DETAILED DESCRIPTION OF THE INVENTION

Figures 1, 3A, 3B:
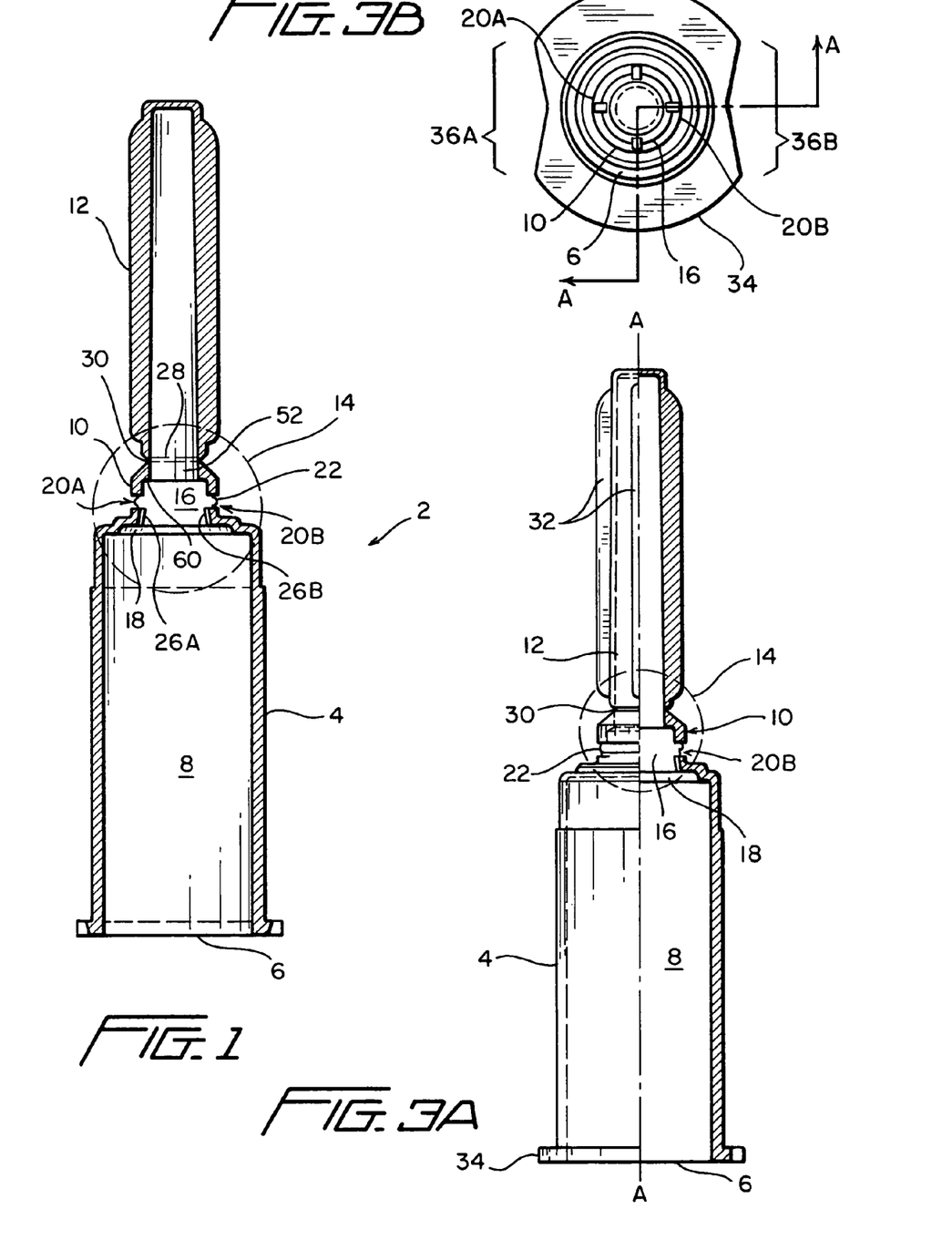

With reference to FIG. 1, a one piece molded vacuum tube holder 2, as shown in cross section, includes a cylindrical body 4 having an opening 6 at its one end dimensioned to receive a conventional fluid storage vacuum tube into the cavity 8 of cylindrical body 4. A neck portion 10 extends integrally from body 4. Extending integrally from neck 10 is an elongate needle cover 12. The one piece vacuum tube holder may be formed by molding and may be made from polypropylene.

Figure 2:
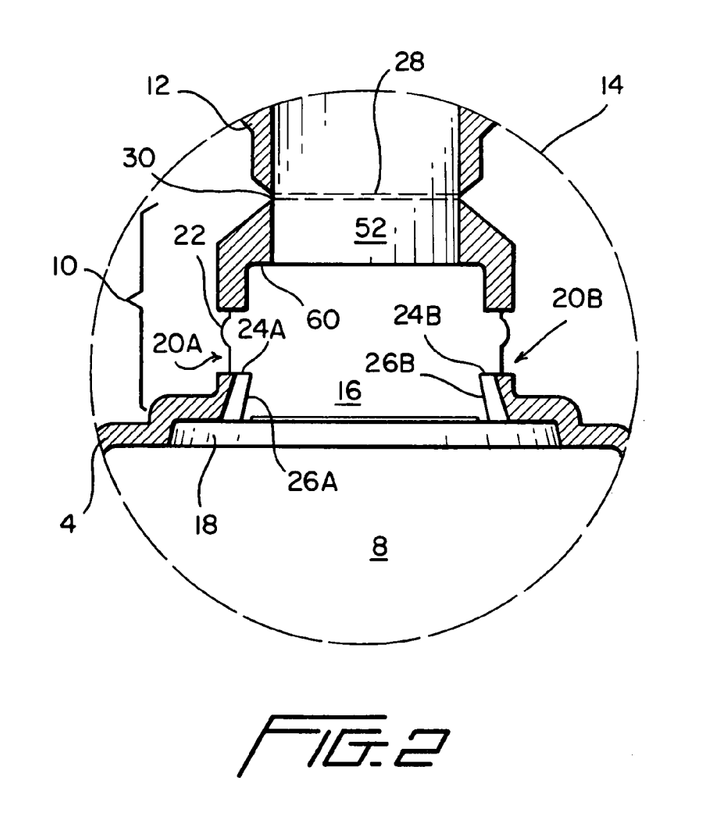
FIG. 2 is an enlarged cross-sectional view of the neck of the vacuum tube holder of FIG. 1.

An exploded view of FIG. 1, designated 14, is shown in FIG. 2.

Figures 5, 9:
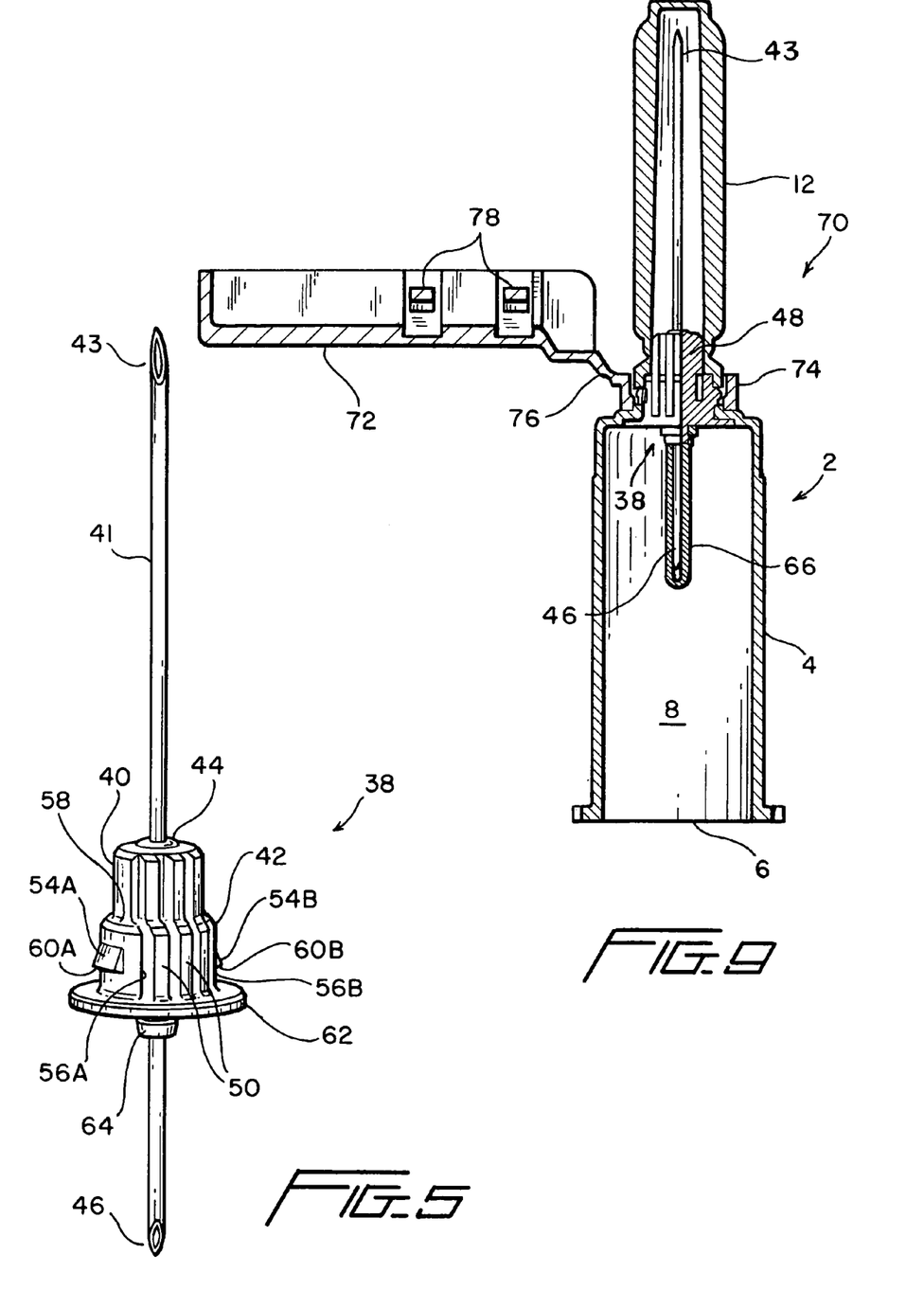
FIG. 5 is a perspective view of a needle hub assembly of the instant invention.
FIG. 9 is a cross-sectional view of the vacuum tube holder assembly of the instant invention.

With reference to both FIGS. 1 and 2, note that neck 10 of the vacuum tube holder 2 has an opening or aperture 16 at its proximal end merging into cavity 8 of body 4. Aperture 16 is dimensioned to accept a needle hub such as that shown in FIG. 5, to be discussed more fully later. At the junction where neck 10 meets with body 4, there is an internal recess 18 to which the base of the needle hub may rest. There are two openings or orifices 20a and 20b formed at the opposite sides, or 180°, at the wall of neck 10. Circumferentially formed about the outer wall surface of neck 10, possibly interrupted by orifices 20a and 20b, is a raised boss or protuberance 22 to which, as will be discussed later, a collar to which a needle protection housing is hingedly connected, as shown in FIG. 9, is rotatably coupled.

As best shown in FIG. 2, the respective lower portions of orifices 20a and 20b are formed by lower supports or ledges 24a and 24b. Ledges 24a and 24b also form the respective tops of ramps 26a and 26b that upwardly extend at an angle from the ceiling of recess 18 formed at the junction joining body 4 to neck 10. Ramps 26a and 26b assist in the fitting of the needle hub, as shown in FIG. 5, to neck 10, as will be discussed infra.

At the distal end of neck 10, i.e., the junction where neck 10 meets elongate needle housing 12, there is a thinning of the material for the vacuum tube holder 2. At this weakened junction or joint, designated by the double dotted line 28, the thinning may be effected by a circumferential notching of the material so that an inward circumferential notch 30 is formed at joint 28. Although remaining one piece during shipping and before use, due to the weakened joint 28, when a predetermined or given torque force is applied to needle cover 12 relative to either neck 10 or body 4, the elongate needle cover 12 could readily be separated or removed, at joint or junction 28, from the remainder portion of vacuum tube holder 12.

Given that the vacuum tube holder 2 is molded in one piece, once separated, elongate needle cover 12 could not be reattached to neck 10. As a result, weakened joint 28 provides a tamper evident seal for the vacuum tube holder 2. In other words, if there is any kind of breakage at joint 28, a user such as a phlebotomist will know that the seal has been broken for that particular vacuum tube holder, and that the needle assembly fitted thereto, to be discussed later, may no longer be sterile or fit for use. To enhance a user's ability to separate elongate needle cover 12 from body 4, a number of elongate ribs 32 extending longitudinally along the outer surface of elongate needle cover 12 are provided during the molding process. See FIG. 3a.

As best shown in the bottom view of FIG. 3b, the proximal end of the cylindrical body 4 is supported by a base 34 which is configured in a semi-elliptical shape so as to allow the placement of the vacuum tube holder against the body of a patient at either side 36a or 36b. Sides 36a and 36b prevent the cylindrical body 4 from rotating and thereby falling off the body, for example the arm of the patient. In addition to showing opening 6, FIG. 3b also shows aperture 16 of neck 10. Moreover, the bottom view of FIG. 3b shows the two orifices 20a and 20b formed at neck 10.

Figure 4:
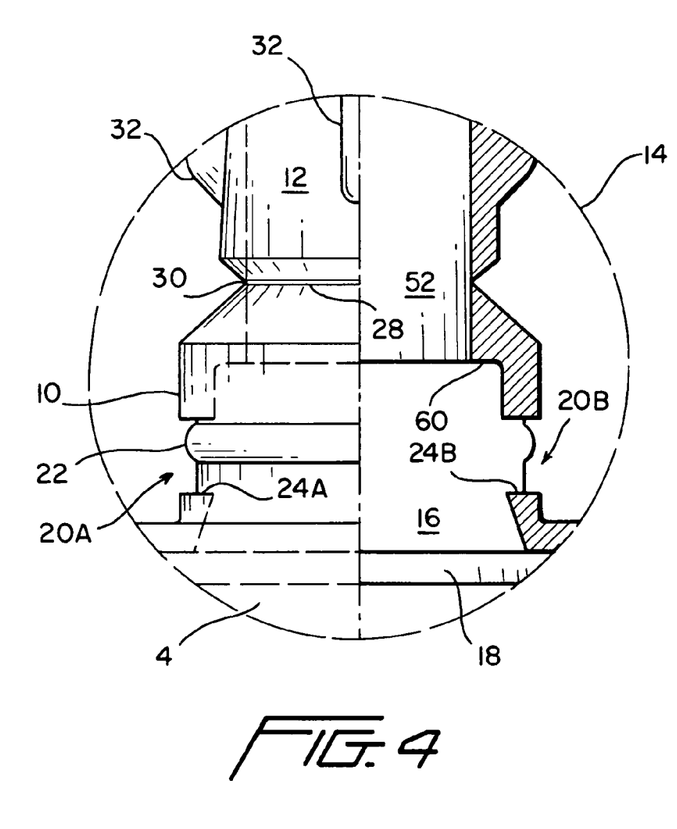

FIG. 4 is an enlarged semi-cross sectional view 14 of FIG. 3a.

Figure 6:
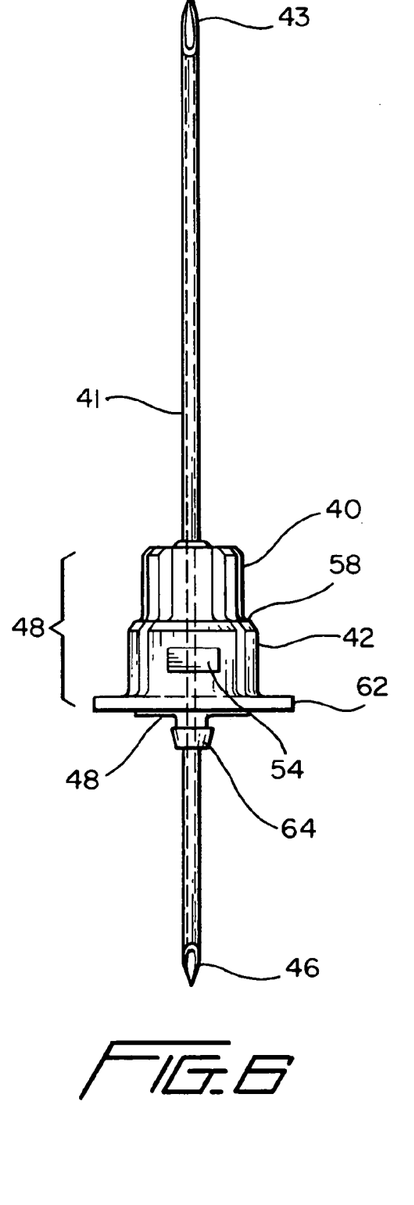
FIG. 6 is a side view of the needle hub assembly.
Figure 7:
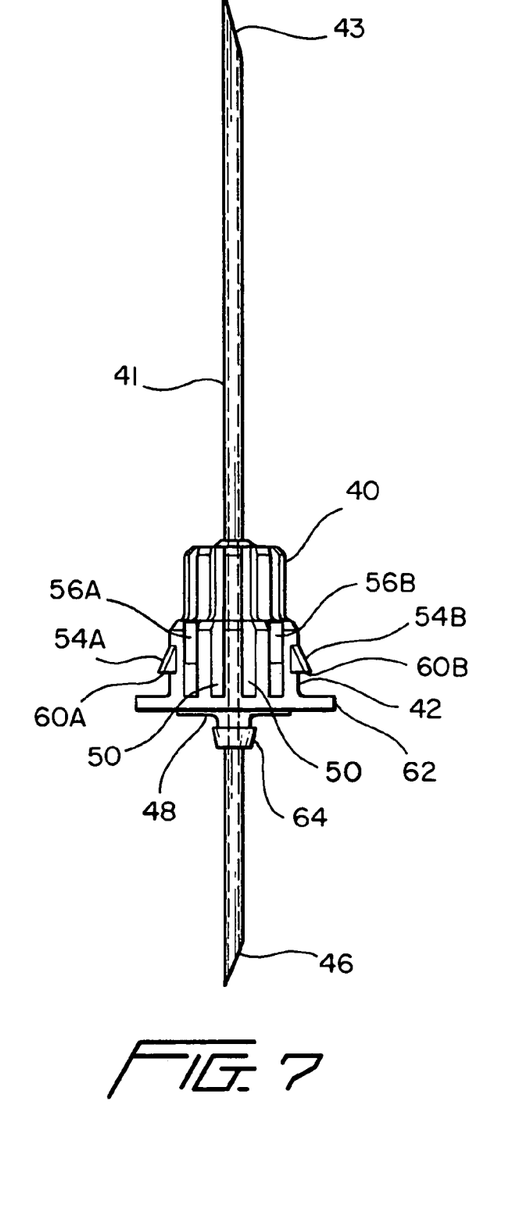
FIG. 7 is another side view of the needle hub assembly.

FIG. 5 is a perspective view of a needle hub assembly 38 that is to be fitted to the vacuum tube holder shown in FIGS. 1-4. With reference also to FIGS. 6 and 7, the needle hub assembly 38 of the instant invention is shown to have a distal section 40 and a proximal section 42. The distal and proximal sections are formed about a double-ended needle 41 having one end 43, which is to be used to prick a patient, extending from the distal end 44 of distal section 40. The other end of the double-ended needle 40, designated 46, extends from the proximal end 48 of proximal section 42. Once properly fitted to vacuum tube holder 2, needle end 43 extends into and is covered by elongate needle cover 12, while needle end 46 extends into cavity 8 of cylindrical body 4. Distal section 40 and proximal section 42 in combination form the needle hub 48 of needle hub assembly 38.

Needle hub 48, at both distal section 40 and proximal section 42, is shown not to be solid, but rather has a number of grooves 50. Grooves 50 are provided in needle hub 48 to possibly lower the cost of manufacturing by eliminating materials that are not needed and also decrease the weight of the needle hub. Distal section 40 of needle hub 48 is dimensioned to have a diameter that fits into the void 52 (FIG. 2) that extends from aperture 16 of neck 10 into the cavity of elongate needle cover 12. Proximal section 42, on the other hand, is dimensioned to fit into the cavity of neck 10 as it is introduced into aperture 16.

Integrally formed at opposite sides, at 180°, of proximal section 42 are catches 54a and 54b. Catches 54a and 54b are assisted by ramps 26a and 26b, when needle hub 48 is press fit to neck 10, after needle hub assembly 38 has been inserted to cavity 8 of body 4. To provide flexibility for catches 54a and 54b so that catches 54a and 54b may move transversely relative to the longitudinal axis of needle hub 48, through slots 56a and 56b are formed in proximal section 48 substantially behind catches 54a and 54b, respectively. A better view of the through slots 56a and 56b may be had with respect to FIG. 10, which is an enlarged view showing the mating of needle hub 48 to neck 10 of the vacuum tube holder. Another view of the through slots 56a and 56b may be had with respect to FIG. 7.

Given that distal section 40 has a smaller diameter than proximal section 42, a ledge 58 is formed circumferentially about needle hub 48 at the intersection of distal section 40 and proximal section 42. Ledge 58 abuts against the bottom of internal shoulder 60 at neck 10, as shown in FIGS. 2 and 4, to prevent distal section 40 from moving further into the cavity of elongate needle cover 12, when needle hub 48 is press fit through aperture 16 into neck 10. Shoulder 60 is designed with sufficient tolerance to allow catches 54a and 54b to be snap fitted to orifices 20a and 20b, respectively, before it abuts ledge 58.

Given the space provided by through slots 56a and 56b, as needle hub 48 is pushed forward into neck 10 via aperture 16, catches 54a and 54b are flexibly compressed by ramps 26a and 26b, until the lowermost portion of those catches move beyond ledges 24a and 24b. At that point, due to their inherent flexibility, catches 54a and 54b would return to their respective original positions with respect to needle hub 48 so that their respective bottom surfaces 60a and 60b rest on and are supported by ledges 24a and 24b. In essence, catches 54a and 54b, acting as one part or portion of a locking mechanism, latch onto orifices 20a and 20b, respectively, which are acting as another part of portion of the locking mechanism, for fixedly retaining needle hub assembly 38 within vacuum tube holder 2. Once thus latched, needle hub 48 is fixedly retained in neck 10 of the vacuum tube holder. To prevent any further forward movement, a base plate 62 integrally forming the proximal end of proximal section 42 is dimensioned to fittingly mate with recess 18 formed at the intersection of neck 10 and body 4. Once mated with recess 18, plate 62 prevents any further forward movement of needle hub 48 toward neck 10.

To enclose needle end 46, which extends into cavity 8 of body 4 of the vacuum tube holder, a barb 64 is integrally formed from the proximal end 48 of proximal section 42. A rubber boot 66 as shown in FIG. 8a and 8b is fitted over needle end 46, with its upper end 68 being fixedly held to barb 64, as is conventionally known.

Figures 8A, 8B, 10:
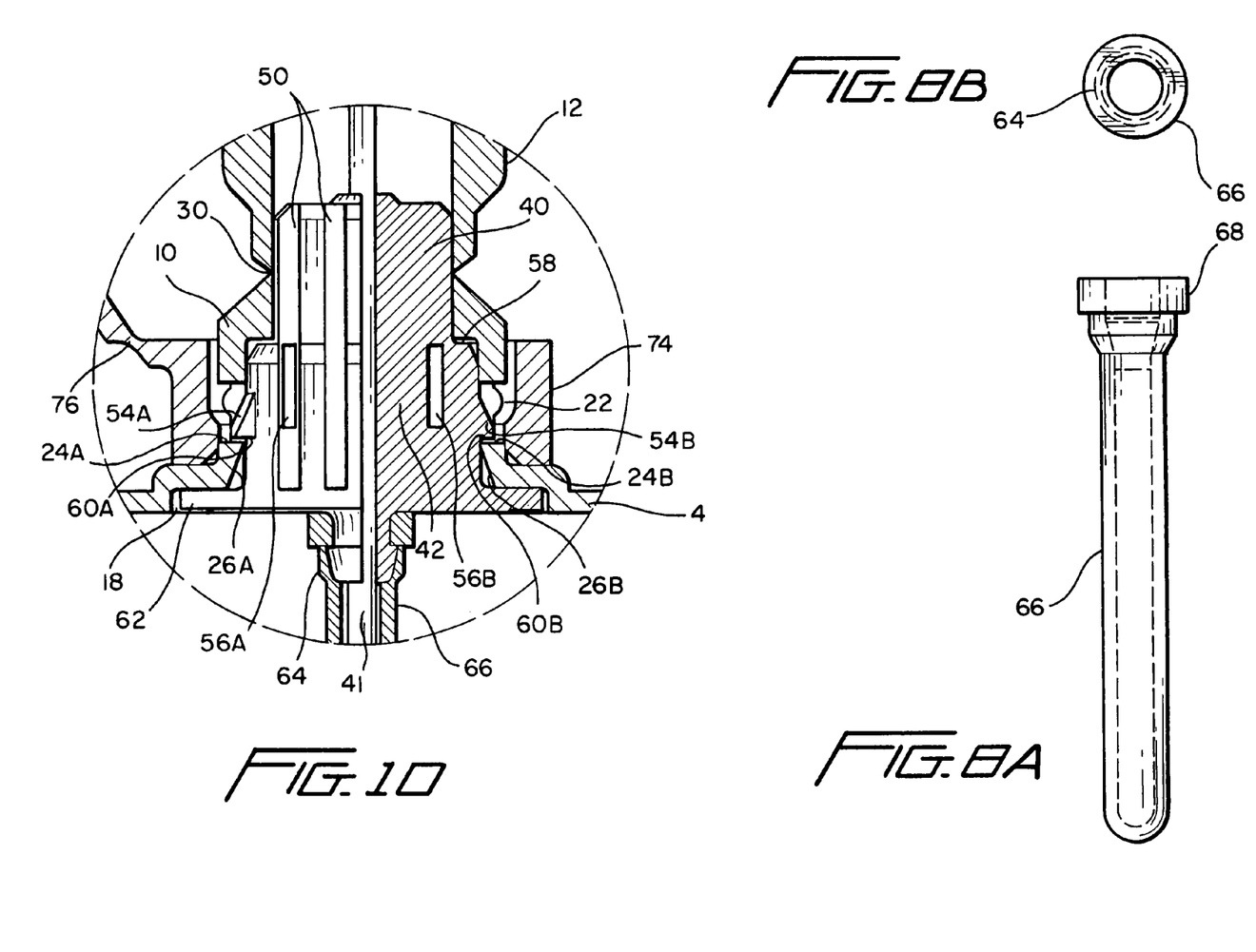

With respect to FIGS. 9 and 10, a completely assembled vacuum tube holder assembly is shown to include the one piece molded vacuum tube holder 2, the one piece molded needle hub assembly 38 fitted to and fixedly held within vacuum tube holder 2, and a safety needle housing 72 rotatably mounted about the neck of vacuum tube holder 2.

In particular, needle housing 72 is flexibly or hingedly attached to a collar or ring 74 by way of a living hinge 76. Needle housing 72 has an elongate slot, not shown, that allows it to pivot over and cover needle end 43, while the needle passes through the slot, after elongate needle cover 12 has been removed from vacuum tube holder 2. There are integral hooks 78 provided in housing 72 for fixedly grabbing end needle 43 once housing 72 has been pivoted to a position in substantial alignment along the longitudinal axis of needle 43, or vacuum tube holder 2. Needle protection housing 72 may also be made from polypropylene A more detailed disclosure of a needle protection housing similar to needle protection housing 72 is given in the aforenoted '285 patent, whose disclosure has been incorporated to the instant specification.

The enlarged view of FIG. 10 shows the needle hub assembly having been fittingly mated to vacuum tube holder 2. More specifically, distal section 40 and proximal section 42 of needle hub assembly 38 are shown to have been mated to neck 10 of the vacuum tube holder and fixedly retained thereat. Moreover, collar 74 is shown to be rotatably mounted about neck 10, at protuberance 22, so that collar 74, and therefore housing 72 attached thereto, is rotatable about neck 10 relative to double-ended needle 41. By design, sufficient friction is provided between protuberance 22 and the internal groove of collar 74 so that collar 74 is not freely rotatable. Thus, to rotate housing 72, a torque force has to be applied thereto.

As was mentioned before, to assemble, the one piece needle hub assembly 38, which may also be made from polypropylene, is first inserted into cavity 8 through opening 6 at the proximal end of the cylindrical body 4 of vacuum tube holder 2. Needle hub 48 of needle hub assembly 38 is then press fit to neck 10 of vacuum tube holder 2 until catches 54a and 54b latch onto orifices 20a and 20b, respectively, formed at the opposite sides of neck 10. Once catches 54a and 54b extend out into orifices 20a and 20b, respectively, their respective bottom surfaces 60a and 60b would act against ledges 24a and 24b of orifices 20a and 20b, respectively. As a result, the needle hub 48 could no longer be moved in a backwards direction, i.e., toward opening 6 of body 4. The ledge 58 formed at the intersection of distal section 40 and proximal section 42 of needle hub 48 and plate 62 formed at the base of proximal section 42 prevent further forward movement of the needle hub. Needle protection housing 72, by way of collar 74 connected thereto, is rotatably mounted about neck 10 of the vacuum tube holder. More specifically, the internal groove of collar 74 is rotatably mated to the protuberance that circumferentially forms about the outer wall surface of neck 10.

To use, a user applies a predetermined torque force to elongate needle cover 12 relative to neck 10 or body 4 to separate the needle cover from neck 10 of the vacuum tube holder, at weakened joint 30. After use and possibly after a vacuum tube inserted into cavity 8 of body 4 which is pierced by end needle 46 has been removed, the contaminated end needle 43 is fixedly held within needle protection housing 72, by the user pivotally moving needle protection housing 72 towards needle end 42 until needle end 43 is grasped by hooks 78 integral in housing 72.

By producing a one piece molded vacuum tub holder, and by press fitting a one piece molded needle hub assembly to the vacuum tube holder, the processing steps for manufacturing the instant inventive vacuum tube holder assembly are made simpler and more economical. If desired, opening 6 of the vacuum tube holder may be sealed with a material that allows sterilization gas to pass through so that the completely assembled device such as that shown in FIG. 9 may be readily sterilized and shipped, without any need for or separate needle cover sheaths and tamper evident warning labels or seals.

The invention claimed is:

1. Apparatus, comprising
a one piece cylindrical body having an opening at one end through which a fluid storage tube is insertable and a neck that has an elongate needle cover extending therefrom, said cover longitudinally extending from said neck at a weakened joint, said cover separable from said neck at said weakened joint when a predetermined torque is applied to said cover relative to said body, said neck having an aperture dimensioned to accept and adaptable to fixedly retain a needle hub; wherein said neck comprises at least one side orifice and said needle hub comprises at least one catch, said catch fixedly latching to said side orifice of said neck when said needle hub is inserted to said neck through said aperture.

2. Apparatus 1, wherein said neck comprises a circumferential protuberance at its outer surface to which a collar of a needle protection housing is rotatably mountable.

3. Apparatus of claim 1, wherein said needle cover, once separated from said neck at said joint, is not attachable back to said neck.

4. Apparatus, comprising: a one piece cylindrical body having an opening at one end through which a fluid storage tube is insertable and a neck that has an elongate needle cover extending therefrom, said cover longitudinally extending from said neck at a weakened joint, said cover separable from said neck at said weakened joint when a predetermined torque is applied to said cover relative to said body, said neck having an aperture dimensioned to accept and adaptable to fixedly retain a needle hub:
wherein said needle hub is a part of a needle assembly comprising a base having a double ended needle extending therethrough, said needle hub including a proximal section having at least one catch and a distal section that is dimensioned to extend from a distal end of said neck when said needle hub is press fitted to said aperture, said catch latching to a side orifice at said neck when said assembly is fully inserted to said aperture.

5. Apparatus, comprising: a one piece cylindrical body having an opening at one end through which a fluid storage tube is insertable and a neck that has an elongate needle cover extending therefrom, said cover longitudinally extending from said neck at a weakened joint, said cover separable from said neck at said weakened joint when a predetermined torque is applied to said cover relative to said body, said neck having an aperture dimensioned to accept and adaptable to fixedly retain a needle hub;

wherein said needle hub is a part of a needle assembly comprising a double ended needle, and wherein once said needle cover is separated from said neck at said joint to expose an end of said needle extending from said needle hub, a needle protection housing pivotally connected to a collar rotatably mounted about said neck is movable to cover said end of said needle to thereby prevent said end of said needle from being further exposed.

6. A needle hub assembly, comprising:
a base having a proximal section and a distal section;
a double ended needle extending through said base so that one end of said needle extends from the distal end of said distal section and an other end of said needle extends from the proximal end of said proximal section; and
at least one catch formed at the outer surface of said proximal section;
wherein said assembly is adaptable to be inserted to the cavity of a cylindrical body through an open end of said body until said catch latches onto an orifice at a neck of said body.

7. Needle hub assembly of claim 6, further comprising:
a circumferential ledge formed at the intersection of said distal and proximal sections, said circumferential ledge maintaining said proximal section within said neck; and
a plate integrally formed at the proximal end of said proximal section, said plate fittingly positioned into a recess formed at a junction of said body where said neck begins, said plate stopping further forward movement of said assembly in the cavity of said body, said assembly being fixedly retained within said body by the latching of said catch to said orifice and the positioning of said plate in said recess.

8. Needle hub assembly of claim 6, further comprising a barb extending from the proximal end of said proximal section in concentric relationship with a portion of said other needle extending from the proximal end of said proximal section, said barb holding an open end of a rubber boot covering said other needle.

9. Needle hub assembly of claim 6, wherein said neck comprises a plurality of orifices, said needle hub assembly further comprising at least two catches transversely formed at opposite sides of said proximal section, said catches each latching onto a corresponding one of said orifices at said neck when said assembly is inserted to the cavity of said cylindrical body through its open end, said body being closed at its other end when said assembly is inserted thereinto.

10. Needle hub assembly of claim 9, wherein said proximal section has a plurality of through slots each formed behind a corresponding one of said catches to provide flexibility for the transverse movements of said corresponding one catch.

11. Needle hub assembly of claim 6, wherein said cylindrical body comprises a one piece body having extending from its neck a needle cover, an area at said body where said neck meets said needle cover being weakened relative to the rest of said body so that said cover is removable from said body when a predetermined torque is applied to said cover relative to said body for exposing said one end of said needle, the aperture of said neck at said area being smaller than the aperture of the rest of said neck.

12. Needle hub assembly of claim 6, wherein said neck of said body comprises a circumferential protuberance at its outer surface whereto a collar of a needle protection housing is rotatably mounted; and wherein once said needle cover is separated from said neck at a weakened joint between said needle cover and said neck to expose said one end of said needle extending from the distal end of said distal section, a needle protection housing pivotally connected to said collar rotatably mounted to said protuberance is adapted to be pivoted in alignment with said needle to cover said one end of said needle.

13. A tube holder assembly, comprising:
a one piece cylindrical body having an opening at one end through which a fluid storage tube is insertable, a neck having one lock mechanism formed to a side thereof, and an elongate cover extending from said neck at a weakened joint of said body; and
a needle assembly having a proximal section and a distal section;
a double ended needle extending through said distal and proximal sections, and
an other lock mechanism formed at the outer surface of said proximal section;
wherein said needle assembly is fixedly fitted within said body with at least said proximal section fitted within said neck and said one and other lock mechanisms in a locking relationship; and
wherein said cover is separable from said neck at said weakened joint when a predetermined torque is applied to said cover relative to either said body or said neck;
wherein said one lock mechanism comprises a pair of orifices formed transversely at opposite sides of said neck and wherein said other lock mechanism comprises a pair of catches formed at opposite sides of the outer surface of said proximal section, each of said catches latching onto a corresponding one of said orifices when said needle hub assembly is inserted to said body and said proximal section is press fitted to said neck; and
wherein said neck has an aperture dimensioned to accept said proximal section and at least a portion of said distal section of said needle assembly.

14. A one piece molded tube holder, comprising: a cylindrical body having a cavity and an opening at one end through which a fluid storage tube is insertable to said cavity, said body including a neck having at least one orifice formed transverse to a side thereof, said neck having an aperture smaller in diameter than said cavity, a needle cover longitudinally extending from said neck away from said body at a weakened joint, whereby said cover is separable from said neck by a predetermined torque being applied to said cover relative to said neck or said body.

15. Tube holder of claim 14, wherein said neck comprises a pair of orifices formed at opposite sides thereof.

16. A one piece molded needle hub assembly to be used with the tube holder of claim 14, comprising: a proximal section and a distal section, said proximal section dimensioned to fit to the aperture of the neck of said container, a double ended needle extending through said distal and proximal sections, a pair of catches formed at opposite sides of the outer circumference of said proximal section, and a through slot formed in said proximal section behind each of said catches to enable flexible movements of said catches transversely to said proximal section.

17. Needle hub assembly of claim 16, further comprising: a circumferential ledge formed at the intersection of said proximal and distal sections, a plate formed at the proximal end of said proximal section, said assembly being mated to said container by said proximal and distal sections being inserted to the cavity of said needle container and then to the aperture of said neck, said circumferential ledge preventing said proximal section from passing through said neck while said catches latch onto respective orifices formed at said neck to fixedly retain said needle hub assembly in place, said plate preventing further movement of said needle hub assembly by mating with a recess internally formed at the base of said neck.

18. A method of manufacturing a one piece holder of fluid storage tubes, comprising the steps of:
   a) forming a cylindrical body having an opening at one end through which a fluid storage tube is insertable into the cavity of said body;
   b) extending from said body a neck having an aperture smaller in diameter than said opening of said body;
   c) providing at least one orifice to a side of said neck for accepting a catch from a needle hub to be inserted into said neck; and
   d) joining an elongate needle cover longitudinally to said neck in a direction away from said body.

19. Method of claim 18, further comprising the step of:
weakening the junction where said needle cover is joined to said neck so that a given torque applied to said cover relative to either said neck or said body will separate said needle cover from said neck.

20. A method of manufacturing a needle hub assembly to be assembled to a holder of fluid storage tubes, comprising the steps of:
   a) forming a needle hub having a proximal section and a distal section about a double ended needle with one end of said needle extending from the distal end of said distal section and an other end of said needle extending from the proximal end of said proximal section;
   b) forming a circumferential ledge at the intersection of said distal and proximal sections;
   c) forming at least one catch at a side of said needle hub, said catch to be latching to a corresponding orifice at a neck of said holder for fixedly retaining said needle hub assembly within said holder.

21. A method of manufacturing a safety holder of fluid storage tubes, comprising the steps of:
   a) forming as a one piece component
      I) a cylindrical body having an opening at one end through which a fluid storage tube is insertable into the cavity of said body,
      ii) a neck having an aperture smaller in diameter than said opening of said body extending from said body,
      iii) one lock mechanism provided to a side of said neck, and
      iv) an elongate needle cover joined to said neck in a direction away from said body;
   b) forming a one piece needle assembly including
      I) a needle hub,
      ii) a double ended needle with one end of said needle extending from a distal end of said needle hub and an other end of said needle extending from a proximal end of said needle hub, and
      iii) an other lock mechanism provided at said needle hub;
   c) inserting said needle hub to the cavity of said body through said opening of said body; and
   d) press fitting said needle hub to said aperture of said neck until said one and other lock mechanisms coact to fixedly hold said needle hub to said neck with said one end extending into said needle cover.

22. Method of claim 21, further comprising the step of:
weakening the junction where said needle cover joins said neck so that a given torque applied to said cover relative to either said neck or said body separates said needle cover from said neck.

23. Method of claim 21, wherein said step (a)(iii) comprises the step of forming a pair of orifices at opposite sides of said neck and said step (b)(iii) comprises the step of forming a pair of catches at opposite sides of said needle hub; and
   wherein said step (d) further comprises the step of press fitting said needle hub into said aperture of said neck until said catches each latch onto a corresponding one of said orifices to thereby fixedly retain said needle hub to said neck.

24. Method of claim 23, further comprising the step of forming a through slot behind each of said catches to provide flexibility for the transverse movements of said each catch.

25. Method of claim 21, further comprising the steps of:
forming a proximal section and a distal section for said needle hub;
forming a circumferential ledge at the intersection of said proximal and distal sections, said ledge preventing said proximal section from being moved out of said neck; and
forming a plate integrally at the proximal end of said proximal section, said plate preventing further forward movement of said needle hub once said needle hub is properly fitted to said neck.

* * * * *